United States Patent
Biber et al.

(10) Patent No.: US 9,395,427 B2
(45) Date of Patent: Jul. 19, 2016

(54) ACTIVATION OF TRANSMIT/RECEIVE ARRAYS FOR DECOUPLING DURING TRANSMISSION

(71) Applicants: Stephan Biber, Erlangen (DE); Klaus Huber, Effeltrich (DE)

(72) Inventors: Stephan Biber, Erlangen (DE); Klaus Huber, Effeltrich (DE)

(73) Assignee: Siemens Aktiengesellschaft, München (DE)

( * ) Notice: Subject to any disclaimer, the term of this patent is extended or adjusted under 35 U.S.C. 154(b) by 532 days.

(21) Appl. No.: 13/960,791

(22) Filed: Aug. 6, 2013

(65) Prior Publication Data

US 2014/0043029 A1 Feb. 13, 2014

(30) Foreign Application Priority Data

Aug. 7, 2012 (DE) .................... 10 2012 213 995

(51) Int. Cl.
*G01R 33/36* (2006.01)
*A61B 5/055* (2006.01)

(52) U.S. Cl.
CPC ............... *G01R 33/36* (2013.01); *A61B 5/055* (2013.01); *G01R 33/365* (2013.01)

(58) Field of Classification Search
CPC .............................. G01R 33/36; G01R 33/365
See application file for complete search history.

(56) References Cited

U.S. PATENT DOCUMENTS

| | | | |
|---|---|---|---|
| 4,825,162 A | 4/1989 | Roemer et al. | |
| 5,144,244 A | 9/1992 | Kess | |
| 5,708,361 A | 1/1998 | Wang et al. | |
| 7,151,373 B2 | 12/2006 | Reykowski | |
| 2003/0028094 A1 | 2/2003 | Kumar et al. | |
| 2004/0124840 A1 | 7/2004 | Reykowski | |
| 2009/0128154 A1 | 5/2009 | Chu et al. | |
| 2010/0145217 A1 | 6/2010 | Otto et al. | |
| 2012/0025832 A1 | 2/2012 | Schmidig | |
| 2012/0098540 A1 | 4/2012 | Biber et al. | |
| 2012/0268133 A1 | 10/2012 | Peter et al. | |
| 2015/0008926 A1* | 1/2015 | Yang ............... | G01R 33/3685 324/322 |

FOREIGN PATENT DOCUMENTS

| | | |
|---|---|---|
| CN | 101435856 A | 5/2009 |
| CN | 101951832 A | 1/2011 |
| CN | 102565732 A | 7/2012 |

(Continued)

OTHER PUBLICATIONS

German Office Action dated May 2, 2013 for corresponding German Patent Application No. DE 10 2012 213 995.8 with English translation.

(Continued)

*Primary Examiner* — Rodney Bonnette
(74) *Attorney, Agent, or Firm* — Lempia Summerfield Katz LLC

(57) ABSTRACT

A system for electromagnetic excitation of an object under examination during magnetic resonance tomography includes a radio frequency (RF) device for generating a radio-frequency signal and a plurality of antennas for emitting the radio-frequency signal. A signal connection exists between the output of the RF device and the plurality of antennas. A source impedance of the signal connection to the output of the RF device at a connection point of the plurality of antennas is significantly higher than the impedance of the plurality of antennas at the connection points, so that the plurality of antennas are fed in a current source feed mode if a radio-frequency signal is present.

20 Claims, 4 Drawing Sheets

(56) References Cited

FOREIGN PATENT DOCUMENTS

| DE | 102010042633 | 4/2012 | | |
|---|---|---|---|---|
| EP | 2413155 A1 | 2/2012 | | |
| NL | EP 0569091 A1 * | 11/1993 | ......... | G01R 33/3628 |
| WO | 2008078239 | 7/2008 | | |
| WO | 2011054923 | 5/2011 | | |

OTHER PUBLICATIONS

Chinese Office action for related Chinese application No. 2013103331177, dated Jul. 1, 2015, with English Translation.

* cited by examiner

ACTIVATION OF TRANSMIT/RECEIVE ARRAYS FOR DECOUPLING DURING TRANSMISSION

This application claims the benefit of DE 10 2012 213 995.8, filed on Aug. 7, 2012.

BACKGROUND

The present embodiments relate to a system for electromagnetic excitation of an object under examination during magnetic resonance tomography with an RF device.

A conventional magnetic resonance tomography apparatus may have a magnet for generating a static magnetic field and also gradient field coils for generating variable magnetic gradient fields in all three spatial axes, which may be superimposed on the static magnetic field. The hydrogen nuclei aligned in the magnetic fields are excited by an RF device for generating RF excitation signals in the form of pulses and antennas for emitting these pulses into a volume in the magnetic field in which the sample is located. The density and the ambient conditions of the hydrogen nuclei in the sample are determined via an RF response signal that the hydrogen nuclei emit because of precession in the magnetic field as a response to the excitation pulses. The RF response signal is captured by antennas and processed in the RF device. Body coils that surround the volume with the sample may be used both as transmit and receive antennas.

In order to increase the receive sensitivity for small objects under examination (e.g., during examination of limbs or of the head), which only partly fill out the sample volume, it is known, for example, from U.S. Pat. No. 4,825,162 to dispose a plurality of receive coils directly on the object under examination. The receive coils are disposed overlapping so that the signal of a neighboring coil is just canceled out in a selected coil. The signals are "orthogonal" to one another and may be processed independently of one another for a volume of the object under examination lying therebelow in each case. To decouple next-but-one neighbors, preamplifiers with low-impedance inputs are provided.

From publications WO 2008/078239 A1 and WO 2011/054923 A1 it is additionally known (e.g., through geometrical arrangement and extensions on the coils that project sideways from the coils and in each case overlap with an extension of the coil-after-next) to also achieve a suppression of the interaction with the next-but-one neighbor in each case. This suppression is also effective for the use of the coils as transmit antennas for the excitation signal.

The respective arrangements suppress the neighbor-neighbor interactions in each case for a specific geometry (e.g., for a flat arrangement). In some cases, however, it is also necessary to arrange the coils spatially around an object under examination (e.g., a knee). In addition, the object under examination, through dielectric and magnetic properties, influences the electrical and magnetic field distributions, so that the signals from the neighboring coils are not completely suppressed.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a magnetic resonance tomograph that also reduces disturbances caused by signals of neighboring coils or antennas for different geometrical arrangements is provided.

The system for electromagnetic excitation of an object under examination during magnetic resonance tomography has an RF device for generating a radio-frequency signal and a plurality of antennas for emitting the radio-frequency signal. The system also has a signal connection between an output of the RF device and the plurality of antennas. A source impedance of the signal connection with the output of the RF device at connection points of the antennas is significantly higher than the impedance of the antennas at the connection points, so that the antennas are fed during the presence of a radio-frequency signal in a current source feed mode.

The system for electromagnetic excitation includes a number of advantages. The mismatching of the impedances of antenna and signal feed at the connection point leads to the antenna being operated in a current source feed mode. In this mode, the current flowing through the antenna is essentially defined by the current delivered from the current source. The current in the antenna is consequently essentially independent of the voltage delivered by the signal line at the connection point. For example, the current through the antenna is thus essentially dependent on an opposing voltage induced in the antenna, which, for example, may emanate from the interaction with a neighboring antenna. If the current flowing through the antenna is independent, then, for example, for a coil as antenna, the magnetic and electric alternating field generated is also essentially independent of the neighboring antennas.

The coupling of the antennas in current feed mode corresponds to a forced oscillation with strong coupling, so that the oscillation is essentially determined by the oscillation coupled in by the RF device and is scarcely influenced by the other antennas. The phase and amplitude dependence of the oscillation in the antenna is also only determined to a slight extent by the resonant frequency of the antenna itself, so that the influence, for example, of the temperature of a medium in the field of the antenna is low. In this case, the output of the RF device may be configured to optionally also supply a body coil with an output signal that is to have a high input power. Therefore, even with a mismatching of the antennas, which are small by comparison with the body coil, a supply with sufficient power to excite the sample is provided.

In one embodiment, the source impedance of the signal connection with the output of the RF device at the terminal points of the antennas may be higher by at least a factor of 2 than the impedance of the antennas at the connection points. Such a ratio has the advantage that the disruptive influence of a neighboring antenna will be reduced by half.

In one embodiment, the RF device may have an input for processing a receive signal, and the system may have a switch and a signal connection between an input of the RF device and the plurality of antennas. In this case, the switch is configured to connect the antennas optionally with the output of the RF device.

The switch advantageously makes it possible to connect the antennas both with the output of the RF device in order to supply the antennas with an RF signal for exciting the sample, and also to disconnect the antennas from the output of the RF device in order to receive a signal of the sample as a response to the excitation. In this way, the received signal may emanate from the excited volume, so that even a number of coils may be operated in parallel. The sensitivity is also at a maximum through the proximity of transmit antenna and receive antenna to the sample.

In an embodiment, a connection impedance of the signal connection with the input of the RF device at the connection point of the antennas may be significantly higher than the antenna impedance at the connection points.

In an embodiment, the connection impedance of the signal connection with the input of the RF device at the connection point of the antennas may be higher at least by a factor of 2 than the impedance of the antennas at the connection points.

In this way, it is advantageously possible to have the antenna connected with the input of the RF device during transmission without withdrawing significant transmit power from the antenna.

In an embodiment, the system may have an RF activation matrix that is configured to distribute the radio-frequency signal from the output of the RF device to the connection point of the antennas with a predetermined impedance and with a predetermined phase offset for each antenna in each case.

Using the predetermined impedance at the connection point, impedance ratios may be set for each antenna and thus in an advantageous manner in accordance with one or more of the present embodiments to reduce crosstalk between the antennas.

In an embodiment, an arrangement of the antennas and the predetermined phase offsets may be configured such that the antennas generate a circular polarized electromagnetic alternating field.

The individual antennas may be supplied from an RF device with RF pulses of a predetermined phase angle, so that through the sum of the electromagnetic alternating fields of the individual antennas, a resulting electromagnetic alternating field, for example, with a circular polarization may be generated. This may be suitable for exciting nuclear resonance.

In one embodiment, the antennas may be antenna coils. Because of short-circuited construction, coils are insensitive to electric charges and do not produce any electrical field peaks that may lead to a patient being endangered. The emission direction of an antenna coil resting on the sample is aligned to the sample at right angles to the plane of the antenna coil (e.g., for a flat coil that lies practically in one plane) and may excite the volume in the sample in this way. For antenna coils lying alongside one another, the respectively excited areas of the sample are divergent (e.g., the antenna coils are "orthogonal" to one another in relation to the sampled areas). Orthogonal here is not to be understood in the geometrical sense but in the sense of signal processing.

In one embodiment, surfaces of the antenna coil may overlap such that the interaction of two adjacent surfaces is minimized. By the arrangement of the antenna coils, antenna coils lying next to one another influence each other as little as possible, and signals from antenna coils lying next to one another may be evaluated in parallel without generating artifacts in the tomography.

DETAILED DESCRIPTION

Figure 1:
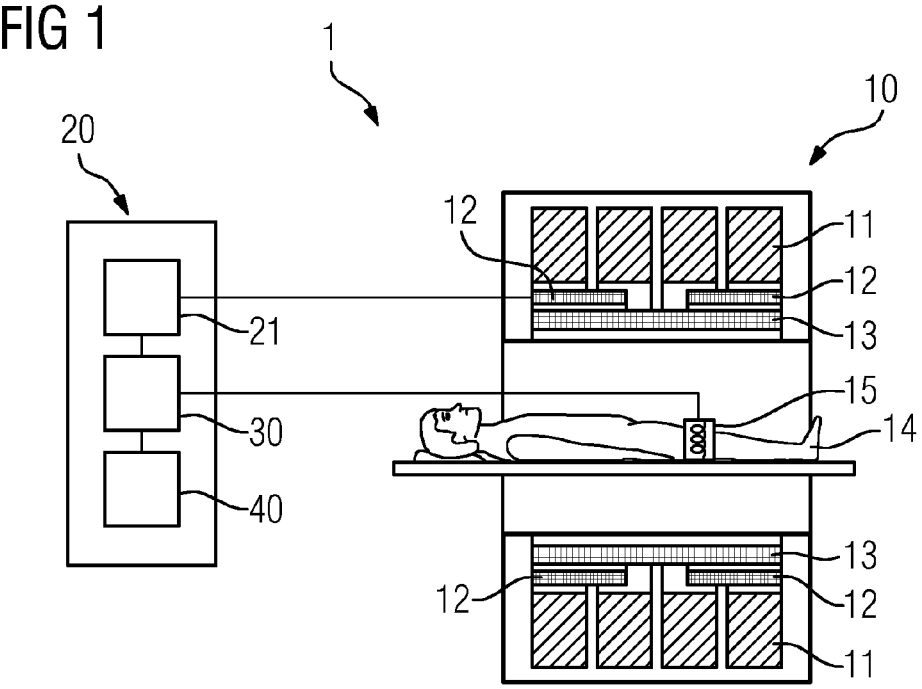
FIG. 1 shows a schematic diagram of one embodiment of a magnetic resonance tomograph.

FIG. 1 shows a schematic diagram of one embodiment of a magnetic resonance tomograph 1. The magnetic resonance tomograph 1 includes a magnet device 10 and a supply device 20.

The magnet device 10 includes superconducting magnets 11 for generating a static magnetic field. The magnet device 10 also includes gradient coils 12 for generating a variable magnetic field gradient in all three spatial directions. A body coil 13 may also be disposed in the magnet device 10. The body coil is configured to generate an electromagnetic alternating field in a volume enclosed by the superconducting magnets 11. The body coil 13 may also be used to measure a magnetic resonance excited by the electromagnetic alternating field in the enclosed volume by the electromagnetic alternating field generated by the magnetic resonance.

In other embodiments, permanent magnets or normally-conducting electromagnets may generate the static magnetic field instead of superconducting magnets 11. As further explained below, the body coil 13 may also be replaced by other antennas.

The magnetic resonance tomograph 1 also has antennas 15 that, in the embodiment shown, are embodied as antenna coils 15 that may be disposed directly on a patient 14 located in the enclosed volume. In one embodiment, the antenna coils 15 may be disposed on a body part such as the knee. This is advantageous if, for example, only a small part of the patient is to be examined with a high resolution. The antenna coils 15 assume the function of the body coil 13 as antennas for receiving the excited alternating field or also as transmit antennas for the exciting electromagnetic alternating field. In such cases, the effect of the antenna coils 15, both as transmit and also as receive antenna, is restricted by comparison with the small volume excited by the body coil 13, which is predetermined by the geometry of the antenna coils 15. If the antenna coils 15 have a flat, circular or square shape, for example, this excitation or receive volume essentially has a lobe shape that extends at right angles from the flat coil into the space. In this way, spatial inhomogeneities of the static magnetic field outside this excitation or receive volume are not captured during the measurement and do not influence the result. In this way, the resolution is able to be improved.

Figure 2:
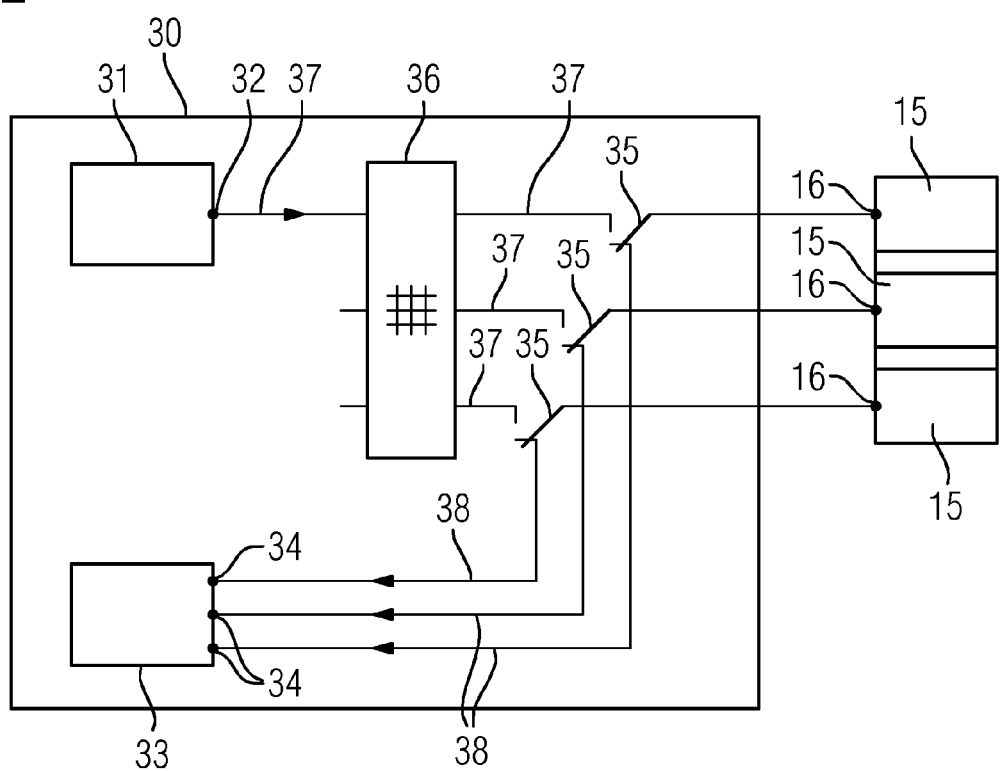
FIG. 2 shows a schematic diagram of one embodiment of a system for electromagnetic excitation.

The lobes of the individual antenna coils 15 do not overlap or overlap only slightly. The individual antenna coils 15 may therefore simultaneously receive or transmit signals for different volumes. The excitation frequencies may be changed in individual antenna coils 15 in order, for example, to compensate for spatial inhomogeneities of the static magnetic field. In order to further reduce the mutual influencing of the antenna coils 15, as indicated in FIG. 2, antenna coils 15 may partly overlap. Since the magnetic field of an antenna coil 15 in the surface surrounded by the antenna coil 15 is precisely opposite the field direction of a stray field in the space to the side of the coil and is significantly stronger, a small overlapping area of two antenna coils 15, with the correct choice of the geometry, may precisely compensate for the interaction by the external stray field. Further options for reduction by circuit technology measures are explained in greater detail in conjunction with FIGS. 3 to 7.

FIG. 2 shows a schematic diagram of one embodiment of a system for electromagnetic excitation of an object under examination. The system includes the antenna coils 15 and an RF device 30. The RF device 30 may be part of a supply device 20 that also includes a gradient control 21 for activating the gradient coils and a control 40 for monitoring the examination and capturing of the measurement data.

The RF device 30 has a pulse generator 31 that, at an RF output 32, provides a radio-frequency pulse suitable for exciting a magnetic resonance. Since the pulse generator 31 of the RF device 30, at the RF output 32, may be configured to supply a body coil 13 with RF pulses, the RF power able to be provided at the RF output 32 is more than sufficient for the smaller antenna coils 15, so that the power losses caused by the explicit mismatching between RF output 32 and antenna coils 15 discussed below have no disadvantageous effect for the antenna coils 15.

Figure 7:
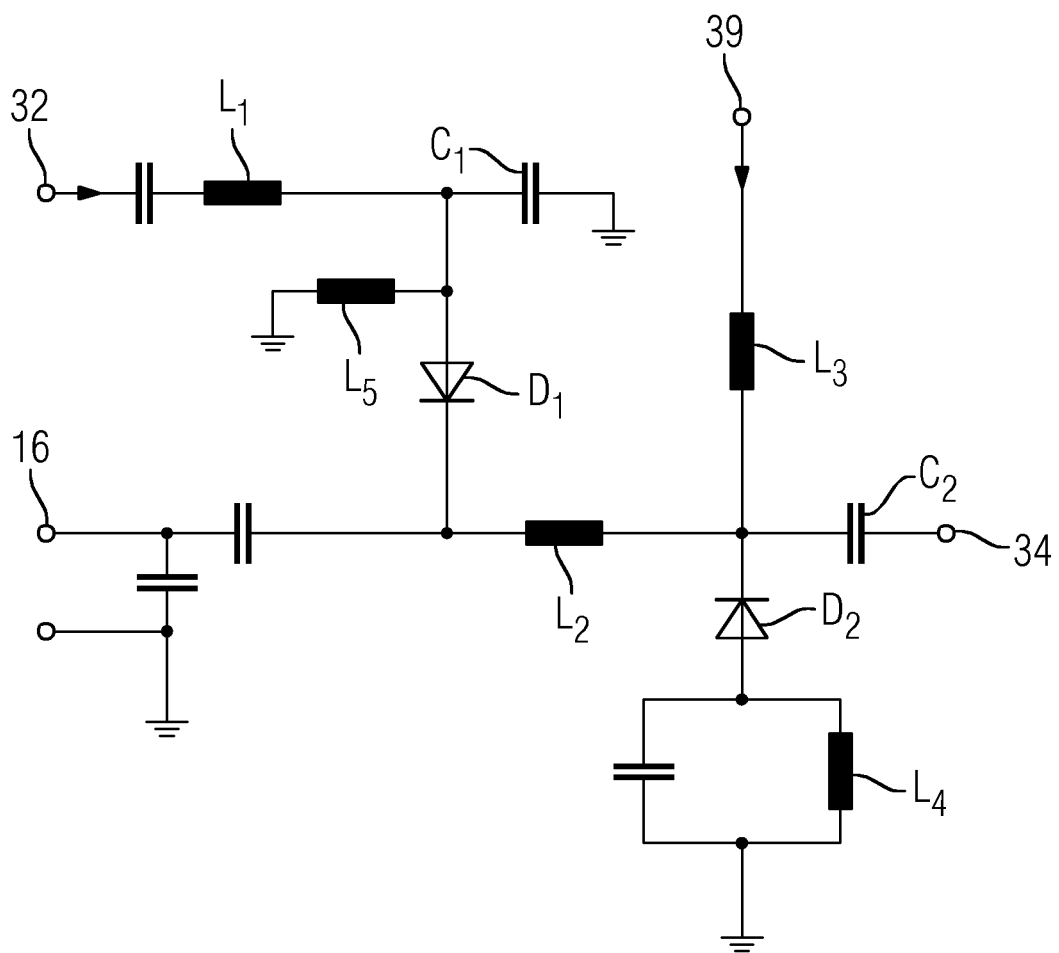
FIG. 7 shows a section from a circuit of one embodiment of a system for excitation.

The radio-frequency pulse is directed via an RF activation matrix 36 and via a switch 35 to the antenna coils 15. Switch 35, RF activation matrix 36 and further electrical connection elements, such as coaxial cables 37, 38, for example, establish a signal connection between RF device 30 and the antenna coils 15. In this case, the switch 35 is provided in an embodiment to, during an emission of the radio-frequency pulse for excitation, make a connection between the RF output 32 and an antenna coil 15 possible, and, during a subsequent receive phase, disconnect the RF output from the antenna coil 15 in order to minimize attenuation of a weak receive signal. A signal connection 38 between RF input 34 and antenna coils 15 during emission of the radio-frequency pulses may be disconnected by the switch 35 in order, for example, to protect the RF input 34 from the high amplitude of the radio-frequency pulse. In one embodiment, as shown in FIG. 7, the signal connections 38 between antenna coils 15 and the RF input 34 may remain in place during the radio-frequency pulses if the RF input 34 is otherwise protected from the effect of the radio-frequency pulse. An attenuation of the radio-frequency pulse by the RF input 34 is to be ignored in this case because of the high power of the radio-frequency pulse. The switch 35 may, for example, be embodied mechanically or, as shown in FIG. 7, electronically.

The RF activation matrix 36 has the task of distributing the radio-frequency pulses to a plurality of antenna coils 15. In this case, the signal may be distributed such that the plurality of antenna coils 15 are activated in a coordinated manner, so that the electromagnetic alternating field generated by the totality of the antenna coils 15 is circular-polarized or at least has a circular-polarized portion in order to provide optimum excitation. For this purpose, a Butler matrix may be used as the RF activation matrix 36, for example. A Butler matrix has a symmetrical number of inputs and outputs. A Butler matrix distributes a signal fed in at an input to the outputs, where the signals at the output are each shifted by a constant phase offset relative to one another. In this way, with a suitable choice of phase offset and the geometrical arrangement of the antenna coils 15, for example, in a circle or polygon, a desired circular polarization of the resulting electromagnetic alternating field may be achieved. In this case, the impedance at the inputs and outputs of the Butler matrix is the same in each case. This may be an impedance widely used in RF technology of 50 ohms.

Just one switch 35 may be provided for all antenna coils 15 together. For example, with an electronic version of the switch 35, as shown in FIG. 2, the function of the switch 35 may be embodied separately for each antenna coil 15. This may be provided directly at a respective connection point 16 of the antenna coils 15. In one embodiment, a plurality of receive units 33 may be provided in order to be able to process receive signals of a number of antenna coils 15 simultaneously.

The system for electromagnetic excitation is able, through switching measures, to reduce the interaction and thus an undesired crosstalk between different antenna coils 15. This will be explained below with reference to FIGS. 3 to 6.

Figure 3:
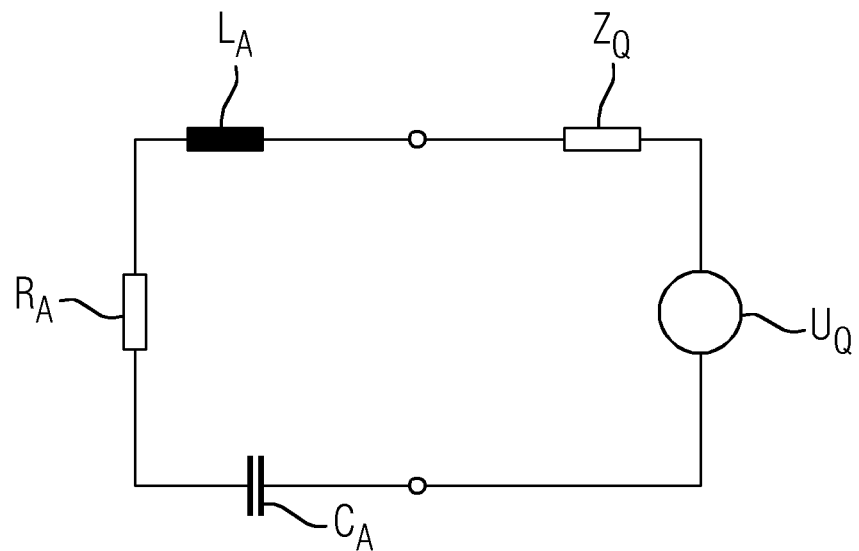
FIG. 3 shows an exemplary equivalent circuit diagram for an individual antenna.

FIG. 3 shows a simplified equivalent circuit diagram for one embodiment of a system. On the left-hand side, an antenna coil 15 is reproduced by the capacitor $C_A$, the resistor $R_A$ and the coil $L_A$. For the subsequent analysis, the standardized complex alternating current resistances of the coil are assumed to be $L_A = i*1$, the resistance $R_A = 1$, and the capacitance $C_A = -i*1$, since the description below only involves the ratio to the values of the source on the right-hand side. These may, for example, be values standardized to a typical antenna and source impedance of 50 ohms. The source is represented in FIG. 3 by a voltage source with the voltage $U_Q$ and the complex source resistance $Z_Q$.

For the resonant frequency of the antenna coil 15, the standardized current is:

$$I = \frac{U_Q}{Z_Q + 1}$$

For $z_{Q0}=1$ and $U_{Q0}=1$, the case of a feed with adapted source, the following applies for a standardized current $I_0 = \frac{1}{2}$.

In one embodiment, the source may have a higher impedance that is realized by a lossless transformation (e.g., transformational or reactive), where n is the transformation ratio, and $$U_Q n \text{ and } Z_Q = n^2 * Z_{Q0} = n^2$$

are produced. The current in the antenna coil 15 as a function of transformation ratio n is then defined as $$I(n) = \frac{n}{n^2 + 1}$$

The current in the antenna coil consequently falls as the transformation ratio rises. The ratio to the current for an injection with adapted source is in this case $$v = \frac{I}{I_Q} = \frac{2n}{n^2 + 1}$$

Figure 4:
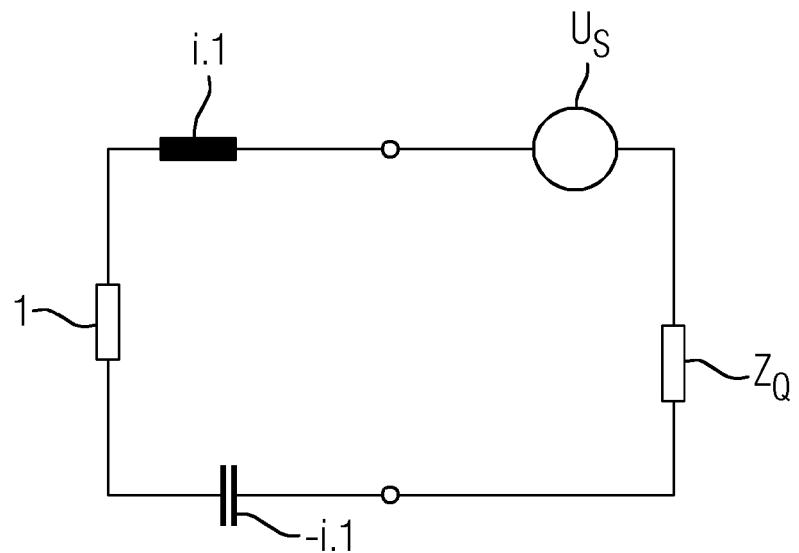
FIG. 4 shows an exemplary equivalent circuit diagram for a fault of an individual antenna induced from outside.

FIG. 4 represents the circuit of FIG. 3 with an additional fault $U_S$ induced from outside. For simplification, the amplitude $U_Q$ of the original source is set to 0, but this has no influence on the following consideration. The current $I_S$ is calculated as $$I_S = \frac{U_S}{1 + Z_Q} = \frac{U_Z}{1 + n^Z}$$

For a feed by an adapted source (e.g., specified with 50 ohms, $Z_Q=1$ in the example), the fault current is $$I_{S0} = \frac{U_S}{2}$$

In general, the fault current suppression t is produced for a feed with higher source impedance $Z_Q$ with $$d = \frac{I_S}{I_{S0}} = \frac{2}{1+n^2}$$

Figure 5:
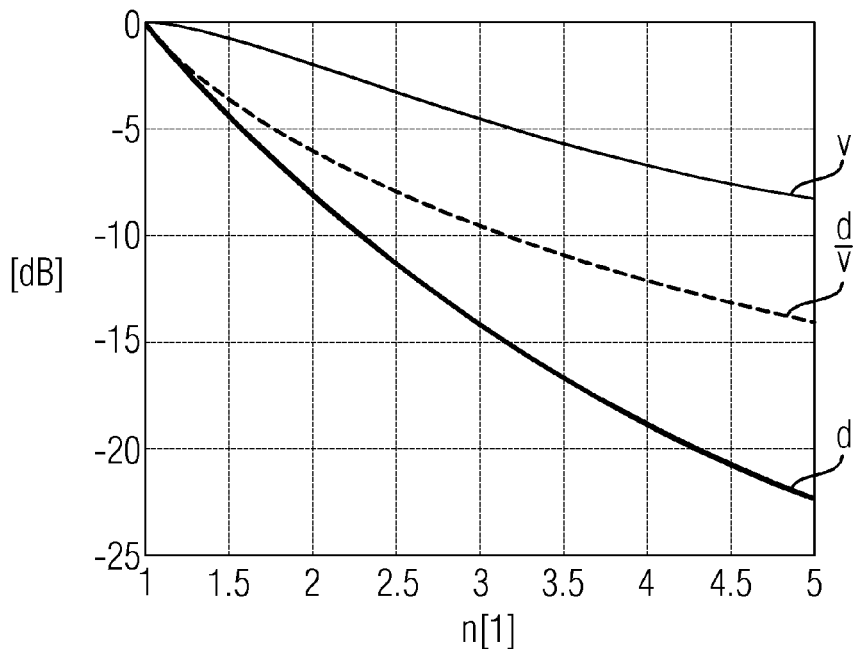
FIG. 5 shows a diagram of exemplary crosstalk attenuation between coils as a function of the mismatching.
Figure 6:
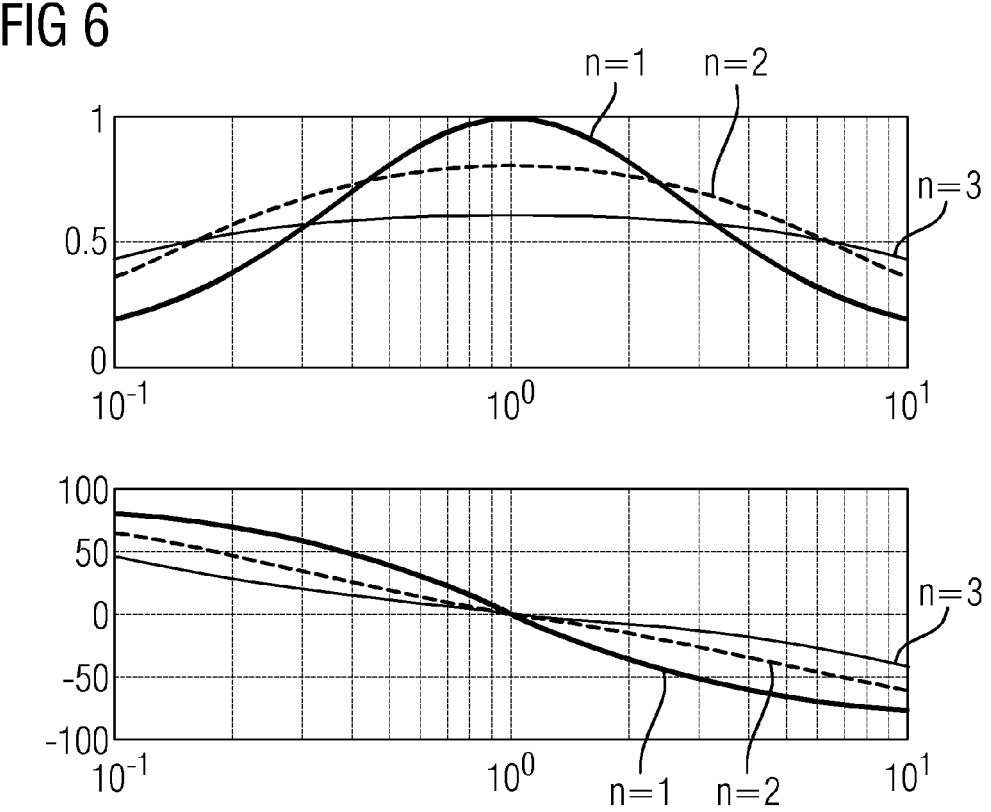
FIG. 6 shows diagrams of exemplary frequency curves and phase curves of a current in a coil for different matching conditions.

Through a transformation of the source impedance, a sensitivity of the current in the antenna coil against external coupling reduced by a factor d may consequently be achieved. FIG. 5 shows in a logarithmic scale the dependencies of λ, d and d/λ on n. The fault current suppression rises significantly more strongly with the source impedance than the field-generating current falls. In addition, the phase relationship of the current is also of significance. Through temperature changes and geometry changes connected thereto or loads on the antenna coil 15 by a medium in the field, the resonant frequency and the phase angle change. In such cases, the effect of these changes is as small as possible. FIG. 6 shows in the upper diagram the amount of the standardized current v on the y axis as a function of the standardized frequency on the x axis. With increasing transformation ratio n, the amount of the normalized current reacts increasingly less sensitively to changes of the resonant frequency.

The same applies to the phase angle that is shown in the lower diagram of FIG. 6.

For plotted n, the y-axis is the phase of the normalized current v as a function of the normalized frequency on the x-axis. The dependence of the phase decreases as the transformation factor n increases.

FIG. 7 shows an exemplary circuit technology realization of the impedance transformation and of the switch 35. Radio-frequency pulses are fed to the circuit from the RF output 32. Through the inductance $L_1$ and $C_1$, an impedance transformation is undertaken for the supplied radio-frequency oscillation. In the example circuit, the feed is to the RF output with an impedance of 50 ohms. The inductance $L_1$ has, for example, a value of 90 nH, and the capacitance $C_1$ has a value of, for example, 22 pF.

During transmission of the radio-frequency pulses for exciting the sample, the radio-frequency energy is conveyed to the connection point 16 of an antenna coil via a PIN switching diode $D_1$, which is connected to ground by a second pole.

Between the radio-frequency pulses, a signal received by the antenna coil 15 is supplied via the connection point 16. Via the inductance $L_2$ and $C_2$, one embodiment of an impedance transformation occurs before the received signal reaches the RF input 34 of the preamplifier of the receive unit 33. In this case, in the typical embodiment shown, the capacitance $C_2$ has a value of 27 pF, and the inductance has a value of 56 nH.

For the desired impedance transformation, depending on the desired transformation ratio, the impedances of the input 34, the output 32 and the antenna coil 15, however, other combinations of values of the capacitances $C_1$, $C_2$ and inductances $L_1$, $L_2$ that achieve the desired effect of the decoupling of the coils may be provided.

The switchover between receive and excitation mode of the circuit is undertaken by PIN diodes $D_1$ and $D_2$, which in one or more of the present embodiments, are of type DH80120 made by Temex. The switchover is made under the control of a switching signal that is fed to a switching input 39 with potential reference to ground and is distributed via the further inductances $L_3$, $L_2$ in the circuit to the diodes. A low-frequency ground reference of the control signal is established via further inductances $L_4$ and $L_5$. The inductances $L_3$, $L_4$ and $L_5$ through their impedance prevent the RF signals to the diodes being diverted to ground or to the potential of the control voltage. In one embodiment, an inductance value for $L_3$, $L_4$ and $L_5$ is 3 µH. The PIN diodes $D_1$, $D_2$ change blocking layer capacitance and thus impedance for the radio-frequency signals as a function of the voltage applied, where the desired switching effect is achieved.

Although the invention has been illustrated and described in detail on the basis of the exemplary embodiments, the invention is not limited by the disclosed examples, and other variations may be derived herefrom by the person skilled in the art without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A system for electromagnetic excitation of an object under examination during magnetic resonance tomography, the system comprising:
    a radio frequency (RF) device configured to generate a radio-frequency signal;
    a plurality of antennas configured to emit the radio-frequency signal; and
    a signal connection between an output of the RF device and the plurality of antennas,
    wherein a source impedance of the signal connection with the output of the RF device at connection points of the plurality of antennas is higher than an impedance of the plurality of antennas at the connection points, so that the plurality of antennas are fed in a current source feed mode when the radio-frequency signal is present.

2. The system as claimed in claim 1, wherein the source impedance of the signal connection with the output of the RF device at the connection points of the plurality of antennas is higher by at least a factor of 2 than the impedance of the plurality of antennas at the connection points.

3. The system as claimed in claim 2, wherein the RF device further comprises an input operable to process a receive signal,
    wherein the system further comprises a switch and a signal connection between an input of the RF device and the plurality of antennas, and
    wherein the switch is configured to optionally connect the plurality of antennas to the output of the RF device or to disconnect the plurality of antennas from the output of the RF device.

4. The system as claimed in claim 1, wherein the RF device further comprises an input operable to process a receive signal,
wherein the system further comprises a switch and a signal connection between an input of the RF device and the plurality of antennas, and
wherein the switch is configured to optionally connect the plurality of antennas to the output of the RF device or to disconnect the plurality of antennas from the output of the RF device.

5. The system as claimed in claim 4, wherein a connection impedance of the signal connection to the input of the RF device at the connection points of the plurality of antennas is higher than the antenna impedance at the connection points.

6. The system as claimed in claim 5, wherein the connection impedance of the signal connection to the input of the RF device at the connection points of the plurality of antennas is higher by at least a factor of 2 than the impedance of the plurality of antennas at the connection points.

7. The system as claimed in claim 1, further comprising an RF activation matrix configured to distribute the radio-frequency signal from the output of the RF device to the connection points of the plurality of antennas with a predetermined impedance and a respective predefined phase offset for each antenna of the plurality of antennas.

8. The system as claimed in claim 7, wherein an arrangement of the plurality of antennas and the predefined phase offset are configured such that the plurality of antennas generate a circular-polarized electromagnetic alternating field.

9. The system as claimed in claim 1, wherein the plurality of antennas are antenna coils.

10. The system as claimed in claim 9, wherein surfaces of the plurality of antenna coils overlap such that an interaction of two neighboring surfaces is minimized.

11. A magnetic resonance tomograph comprising:
a system for electromagnetic excitation of an object under examination during magnetic resonance tomography, the system comprising:
a radio frequency (RF) device operable to excite a radio-frequency signal;
a plurality of antennas operable to emit the radio-frequency signal; and
a signal connection between an output of the RF device and the plurality of antennas,
wherein a source impedance of the signal connection with the output of the RF device at connection points of the plurality of antennas is higher than an impedance of the plurality of antennas at the connection points, so that the plurality of antennas are fed in a current source feed mode when the radio-frequency signal is present.

12. The magnetic resonance tomograph as claimed in claim 11, wherein the source impedance of the signal connection with the output of the RF device at the connection points of the plurality of antennas is higher by at least a factor of 2 than the impedance of the plurality of antennas at the connection points.

13. The magnetic resonance tomograph as claimed in claim 12, wherein the RF device further comprises an input operable to process a receive signal,
wherein the system further comprises a switch and a signal connection between an input of the RF device and the plurality of antennas, and
wherein the switch is configured to optionally connect the plurality of antennas to the output of the RF device or to disconnect the plurality of antennas from the output of the RF device.

14. The magnetic resonance tomograph as claimed in claim 11, wherein the RF device further comprises an input operable to process a receive signal,
wherein the system further comprises a switch and a signal connection between an input of the RF device and the plurality of antennas, and
wherein the switch is configured to optionally connect the plurality of antennas to the output of the RF device or to disconnect the plurality of antennas from the output of the RF device.

15. The magnetic resonance tomograph as claimed in claim 14, wherein a connection impedance of the signal connection to the input of the RF device at the connection points of the plurality of antennas is higher than the antenna impedance at the connection points.

16. The magnetic resonance tomograph as claimed in claim 15, wherein the connection impedance of the signal connection to the input of the RF device at the connection points of the plurality of antennas is higher by at least a factor of 2 than the impedance of the plurality of antennas at the connection points.

17. The magnetic resonance tomograph as claimed in claim 11, further comprising an RF activation matrix configured to distribute the radio-frequency signal from the output of the RF device to the connection points of the plurality of antennas with a predetermined impedance and a respective predefined phase offset for each antenna of the plurality of antennas.

18. The magnetic resonance tomograph as claimed in claim 17, wherein an arrangement of the plurality of antennas and the predefined phase offset are configured such that the plurality of antennas generate a circular-polarized electromagnetic alternating field.

19. The magnetic resonance tomograph as claimed in claim 11, wherein the plurality of antennas are antenna coils.

20. The magnetic resonance tomograph as claimed in claim 19, wherein surfaces of the plurality of antenna coils overlap such that an interaction of two neighboring surfaces is minimized.

* * * * *